United States Patent
Chang et al.

(10) Patent No.: US 7,411,680 B2
(45) Date of Patent: Aug. 12, 2008

(54) DEVICE FOR COUNTING MICRO PARTICLES

(75) Inventors: Jun Keun Chang, Seoul (KR); Chanil Chung, Kyunggi-Do (KR); Dae Sung Hur, Kyungsangbuk-Do (KR); Alexey Dan Chin-Yu, Seoul (KR); Seok Chung, Seoul (KR); Jeong Ku Hwang, Kangwon-Do (KR); Seung Hwa Jeon, Kangwon-Do (KR)

(73) Assignee: Digital Bio Technology, Seoul (KR)

( * ) Notice: Subject to any disclaimer, the term of this patent is extended or adjusted under 35 U.S.C. 154(b) by 287 days.

(21) Appl. No.: 10/565,162

(22) PCT Filed: Jul. 13, 2004

(86) PCT No.: PCT/KR2004/001736

§ 371 (c)(1),
(2), (4) Date: Jan. 19, 2006

(87) PCT Pub. No.: WO2005/008226

PCT Pub. Date: Jan. 27, 2005

(65) Prior Publication Data

US 2006/0187442 A1 Aug. 24, 2006

(30) Foreign Application Priority Data

Jul. 19, 2003 (KR) .................. 10-2003-0049524
Jul. 8, 2004 (KR) .................. 10-2004-0053031

(51) Int. Cl.
*G01N 33/48* (2006.01)
*G01N 21/63* (2006.01)
*G01N 33/557* (2006.01)

(52) U.S. Cl. .................. 356/432; 356/246; 356/440; 356/39; 436/517

(58) Field of Classification Search .......... 356/432–444, 356/244, 246, 39, 72–73; 250/559.01, 559.09, 250/206.1; 436/517, 528; 422/82.05, 61–63, 422/67
See application file for complete search history.

(56) References Cited

U.S. PATENT DOCUMENTS 4,541,719 A * 9/1985 Wyatt .................. 356/343
4,580,895 A * 4/1986 Patel .................. 356/39

(Continued)

FOREIGN PATENT DOCUMENTS

KR 2001-0017092 A 3/2001

(Continued)

*Primary Examiner*—Sang Nguyen
(74) *Attorney, Agent, or Firm*—Browdy and Neimark

(57) ABSTRACT

A device for counting micro particles is presented. The device comprises a light source; a chip containing micro particles; an object lens; a CCD camera; a counting part; and a shifter for shifting the position of the chip. It is easy to count the number of micro particles, such as red blood cells or somatic cells, by using the device. The shifter shifts the position of the chip by a predetermined distance at every predetermined time interval in order that a certain area adjacent to the area photographed just before is shifted to the point where the light is incident. Therefore, sub-areas on the chip are photographed successively. The counting part counts the number of micro particles in each sub-area, and adds them together to calculate the total number of micro particles in the samples.

10 Claims, 7 Drawing Sheets

U.S. PATENT DOCUMENTS

| | | | |
|---|---|---|---|
| 5,100,805 A * | 3/1992 | Ziege et al. | 436/517 |
| 5,366,867 A | 11/1994 | Kawakami et al. | |
| 5,428,451 A | 6/1995 | Lea et al. | |
| 5,854,684 A * | 12/1998 | Stabile et al. | 356/440 |
| 5,976,892 A | 11/1999 | Bisconte | |
| 6,385,272 B1 | 5/2002 | Takahashi | |
| 6,667,177 B1 | 12/2003 | Yabusaki | |
| 6,696,269 B2 * | 2/2004 | Newell | 435/32 |
| 6,787,364 B2 * | 9/2004 | Tajima et al. | 436/86 |
| 7,280,204 B2 * | 10/2007 | Robinson et al. | 356/318 |
| 7,282,180 B2 * | 10/2007 | Tibbe et al. | 422/82.05 |

FOREIGN PATENT DOCUMENTS

| | | |
|---|---|---|
| KR | 2001-0031949 A | 4/2001 |
| WO | WO 00-39329 A1 | 7/2000 |

* cited by examiner

DEVICE FOR COUNTING MICRO PARTICLES

TECHNICAL FIELD

The present invention relates to a device for counting the number of micro particles such as cells. More specifically, the present invention relates to a device for counting micro particles, which comprises the sample chip wherein a sample containing the particles is located at a reading part; a light source projecting light into a sub-area at the sample chip; an object lens to magnify the image of the sample that is formed at the sub-area; an image photographing part photographing the image of the sample; a micro particle counting part counting micro particles in the sub-area using the photographed image; and the chip shifting part shifting the sample chip.

BACKGROUND ART

For the patients suffer from AIDS, leukemia, or anemia, it is necessary to count the number of particles of leukocyte or erythrocyte related to such disease in the blood of the patients in order to diagnose the diseases, to monitor the progress of the diseases, and to verify the effect of treatment.

Particularly, the blood test is conducted not only for diagnosing the diseases, but also for monitoring the patients proved to suffer from the diseases.

The analysis devices developed for blood analysis, for example, Neucleocounter™ of Chemometec, Denmark, are too expensive, and the operating method is so difficult that it is not easy to use the device for not only the ordinary person, but also the analysis expert. Also, as the sample chip for the analysis device is fabricated separately and is too expensive, it is a burden to use such device.

Under the such circumstance, medical technologists count the number of leukocyte or erythrocyte cells in blood by hand in almost all the hospitals. Since medical technologists count them by hand, the errors in the inspection occur frequently, and it takes much time to inspect.

Therefore, the necessity is high for the device which can count the number of leukocyte or erythrocyte cells in blood promptly and accurately, and can be used in convenience with low cost.

Particularly, in case of collecting and examining patient's urine, cerebrospinal fluid, gastric juice, or ascites, etc., the examination should be done in an hour because of the characteristic of the sample. Thus, the device for counting specific cells in the sample promptly is needed.

Further, in case of using the previously-developed device or counting the cells by hand, there is a problem that a person is likely to expose to a harmful dying reagent in the process of experiment.

DISCLOSURE OF INVENTION

The present invention is suggested to solve the said problems, and the device of the present invention for counting micro particles comprises a chip containing micro particles; a light source; an object lens; an image photographing part; a counting part; and a chip shifter.

It is possible to automatically count the number of micro particles in a sample, such as yeast, lactobacillus, zymogen, animal cells, erythrocytes(red blood cells), leukocytes(white blood cells), or somatic cells, by using the device.

Particularly, the chip shifter shifts the position of the chip by a predetermined distance at every predetermined time interval in order that a certain area adjacent to the area photographed just before by a CCD camera is shifted to the point where the light is incident. Therefore, sub-areas on the chip are photographed successively. The counting part counts the number of micro particles in each sub-area, and adds them together to calculate the total number of micro particles in the samples. Therefore it is possible to count micro particles in the sample promptly and accurately. The structure of the device is simple, and it can be used in convenience, and the price is low, too.

The object of the invention is to provide a device for counting the number of micro particles.

The invention relates to a device for counting the number of micro particles.

More specifically, the invention relates to a device for counting the number of micro particles comprising:

a sample chip wherein a sample containing the particles is located at a reading part;

a light source projecting light into a sub-area on the sample chip;

an object lens facing to the chip to magnify the image of the sample that is formed at the sub-area by the light incident from the light source;

an image photographing part(for example, CCD camera) photographing the image of the sample, which is magnified through the object lens, in a sub-area on the sample chip;

a micro particle counting part counting micro particles on the sub-area from the image photographed by the image photographing part; and a chip shifter shifts the position of the sample chip in order that a certain area adjacent to the area photographed just before is shifted to the point where the light is incident.

In the device according to the invention, the chip shifter shifts the sample chip by a predetermined distance at every predetermined time interval. For example, every time the sub-area on the sample chip where the light is incident is photographed by a CCD camera, the chip shifter shifts the sample chip by a predetermined distance in order that a certain area adjacent to the area photographed just before is shifted to the point where the light is incident.

Since the sample chip is shifted by a predetermined distance at every predetermined time interval, sub-areas on the chip adjacent to the area photographed by a CCD camera just before are photographed successively. Therefore it is possible to photograph all the areas on the sample chip subsequently. The exact position of the sample chip can be controlled at high speed by the chip shifter, for example, X-Y stage of rack/pinion type or ball screw type.

After the micro particle counting part counts micro particles on the sub-area photographed successively by the image photographing part, the counting part can calculate the total number of micro particles in the samples by adding the number of micro particle in each of the sub-area together. Particularly in case that the height of the reading part wherein the sample is contained, and the size of the area of the sub-area photographed by the image photographing part are known, the volume of the reading part can be calculated. Therefore, since the volume of the total area (in the reading part) can be found, the volume of the sample containing micro particles is calculated. So, from the total volume of the sample and the total number of the micro particles, the average density of the micro particles (i.e, the number of micro particles in a unit volume) can be calculated.

Thus, the micro-particle counting device according to the present invention can enhance the precision of counting since it photographs the sample chip by each sub-area and counts the particles. Further, although the micro-particles are maldistributed, there are no errors since it counts all the area of the sample.

In the device of the present invention, a halogen lamp, a xenon lamp, a mercury lamp, an LED, or a laser is selectively used as the light source depending on the property of particles. For example, in case of counting erythrocyte, it is preferable to use the lamp emitting the ultraviolet—visible light, or LED. In case of counting leukocytes or somatic cells containing cell nucleus, it is preferable to use the LASER as the light.

The device according to the invention can further comprise the incident light control lens controlling the amount of light emitted from the light source and the distance of focus onto the sample chip in the front of the light source.

Further, the device according to the invention can further comprise the optical filter which passes the light with a specified wave length between the object lens and the image photographing device. So, it can count the number of particles by selectively passing the light with a specific wavelength that is emitted by a specific particle of the sample particles and photographing them.

The device can comprise plural LASERs, and can further comprise the optical filter exchanger with plural optical filters corresponding to the wavelength of the LASERs. Since the specific optical filter passing the light with a specific wavelength can be selectively used, it is easy to count the desired particles.

The magnification of the object lens can be selectively used as occasion demands. It is preferable to observe at low magnification in order to totally figure out the distribution of particles on the reading part of the sample chip.

However, in case of irradiating with light on each pre-divided sub-area of the sample chip to observe by the image photographing part and the counting part, it is preferable to use the object lens with a high magnification in order for exact counting.

After the image photographed by the image photographing device, for example CCD camera, is transmitted to a computer, it can be possible to count the number of specific particles by executing a image-related program in the micro-particle counting part equipped in the computer. As it is above mentioned, after the micro-particle counting part counts the micro-particles in the sub-area sequently photographed on the sample chip, and it can count all the particles in the sample by adding up the micro-particles of each sub-area. Further, from the total volume of the sample in the reading part and the total number of the micro particles, the average density of the micro particles can be calculated.

In case of photographing erytirocyte by use of the light source of a ultraviolet—visible ray, the erythrocyte is represented in black. Thus, the number of the erythrocyte can be counted by counting the black particles. In case of using the light source of LASER, the leukocytes are dyed with fluorescent dyes and emit light with a specific wavelength. Thus, the number of the leukocyte can be counted by photographing the light with a specific wavelength passing through the optical filter in the light through the object lens.

By using the device, it is possible to immediately count not only the each kind of organization ingredients such as erytirocyte or leukocyte in blood, but also the somatic cells in body fluids and other general micro-particles. Further, by promptly calculating the ratio of the number of specific leukocytes in the total number of leukocytes, it is possible to immediately report the progress of diseases. It can be also used for the examination of cell viability and the count of cell in gene expression.

As it is particularly convenient to use the device, after a sample is dropped into the sample chip, which is equipped with the device according to the invention, the number of micro-particles is automatically counted. Therefore, it is easy for not only experts but also ordinary people to use the device.

DESCRIPTION OF REFERENCE NUMERALS FOR IMPORTANT PART OF THE DRAWINGS

Figure 1:
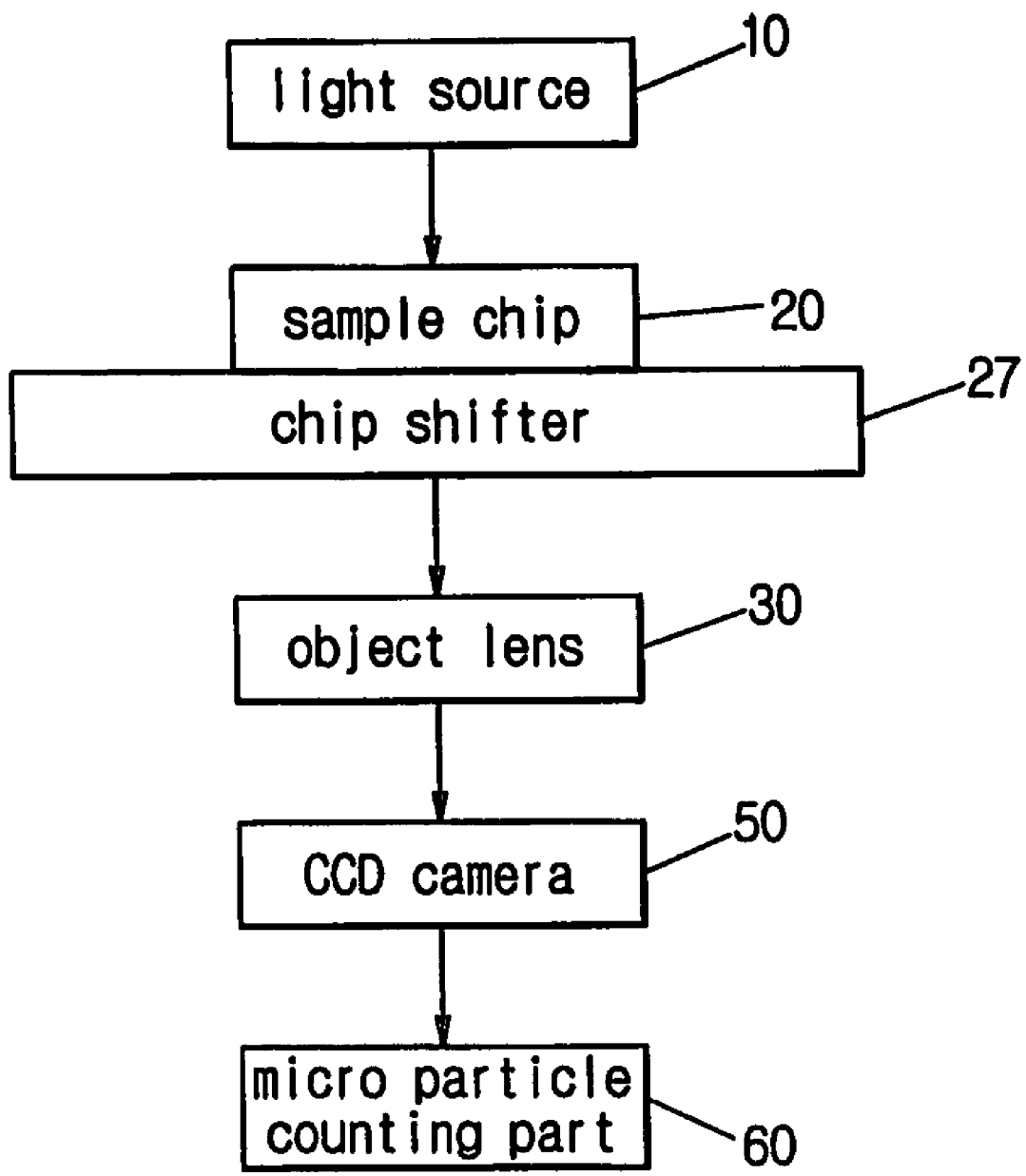
FIG. 1 is a component figure of the micro-particle counting device according to the present invention.

10: lightsource 11a:LED
11b: LASER light source
12a,12b: control lens for incident ray
13a: filter for a incident ray 14,51: reflection mirror
20: sample chip 21: input hole for samples
22: sample vent 23: reading part
24: upper substrate for the sample chip
25: lower substrate for the sample chip
27: shifter for the sample chip 30: object lens
40: optical filter 50: CCD camera
60: counting part for the micro-particles

BEST MODE FOR CARRYING OUT THE INVENTION

Reference will now be made in detail to the present invention as illustrated in the accompanying drawings. However, the invention cannot be confined by the following embodiment.

FIG. 1 is a component figure of the micro-particle counting device according to the present invention.

The device comprises a sample chip(20) wherein a sample containing the particles is located at the reading part with predetermined volume;

a light source(10) projecting light into a sub-area on the sample chip;

an object lens(30) facing to the chip to magnify the image of the sample that is formed at the sub-area by the light incident from the light source;

a CCD camera(50) photographing the image of the sample, which is magnified through the object lens, in a sub-area on the sample chip; and a micro particle counting part counting micro particles on the sub-area photographed by the image photographing part.

The sample chip(20) is placed on a chip shifter(27) which can shift the position of the sample chip in order to shift a certain area to the point where the light is incident. Thus, an area adjacent to the area photographed just before by the CCD camera(50) can be shifted to the point where the light is incident.

The micro-particle counting device can further comprise an optical filter(not illustrated) which passes the light with a specified wave length.

Hereinafter, the operation of the invention will be described in reference to FIG. 1 through FIG. 3.

The light emitted from the light source(10) is incident on a sub-area at the sample chip(20). Wherein the device can further comprise the incident light control lens(not illustrated) controlling the amount of light emitted from the light source(10) and the distance of focus. In addition, the device can further comprise the incident optical filter(not illustrated) which passes the light with a specified wave length, and emits the light onto the sample chip(20).

Figure 2A:
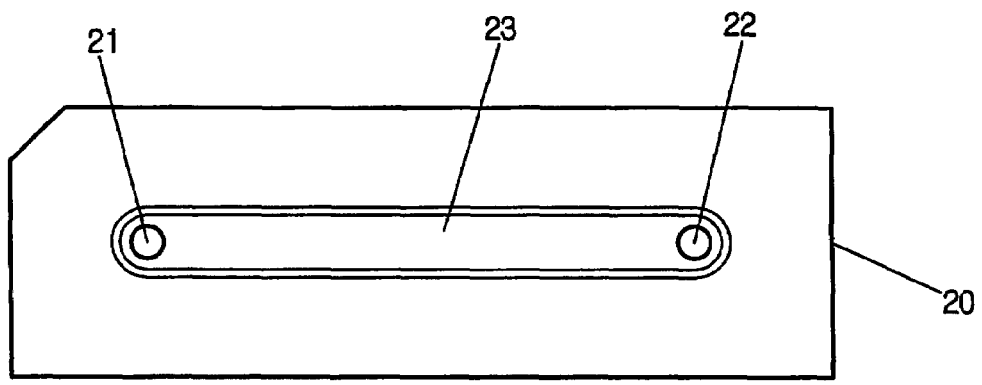
FIG. 2a is a plane figure of the sample chip for containing a sample.
Figure 2B:
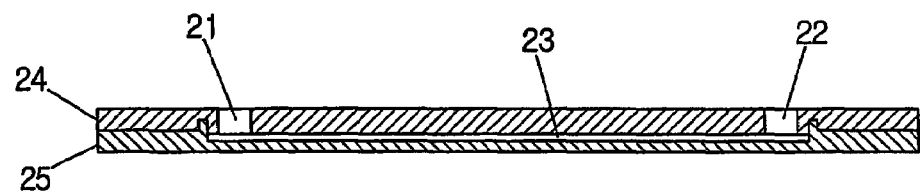
FIG. 2b is a cross-sectional view of the sample chip.

One embodiment of the sample chip for containing a sample is depicted at FIG. 2a and FIG. 2b. FIG. 2a is the plane figure of the sample chip and FIG. 2b is the cross-sectional view of the sample chip.

The sample chip includes an upper substrate(24) and a lower substrate(25). There is a reading part(23) formed in the space between the upper substrate and the under substrate for charging with samples. By forming the reading part(23) with a predetermined height and a predetermined width, the volume of the sample can be known exactly. Preferably, by forming the height of 10 to 100 μm, the micro-particles for the examination is not floated and fixed.

Further, the sample chip(20) is provided with a sample input hole(21) connected to the reading part(23) for inputting samples, and a sample vent(22) for venting the air and excessive amount of the sample inside the reading part(23).

The sample chip(20) is made of plastic and a disposable one can be used conveniently.

If dyeing reagent is coated inside the reading part(23) of the sample chip(20) in order to dye the sample, a user will not be exposed to a harmful dying reagent.

As above mentioned, after charging the reading part(23) with the sample by dropping the sample containing micro-particles on the sample chip(20) through the sample input hole(21), the sample chip(20) is located on the chip shifter(27). Then, the chip shifter(27) shifts the sample chip(20) to the position wherein the light from the light source(10) is incident.

When the light from the light source(10) is incident onto the sub-area in the sample chip(20), the image of the sample is magnified by the object lens(30) facing to the sample chip(20), and the CCD camera(50) photographs the image of the sample that is magnified by the object lens(30).

The device can further comprise the optical filter(not illustrated) which passes the light with a specified wave length in the light passed through the object lens(30). So, by selectively passing the light with a specific wavelength that is emitted by a specific particle in the sample particles, the CCD camera(50) can photograph only the specific particles.

Then the image photographed by the CCD camera(50) is transmitted to the micro particle counting part(60), it can be possible to count the number of specific particles by executing a image-related program in the micro-particle counting part(60) equipped in a computer.

Then, the chip shifter(27) shifts the position of the chip by a predetermined distance in order that a certain area adjacent to the area photographed just before is shifted to the point where the light is incident and micro-particles in the sub-area can be counted.

Figure 3:
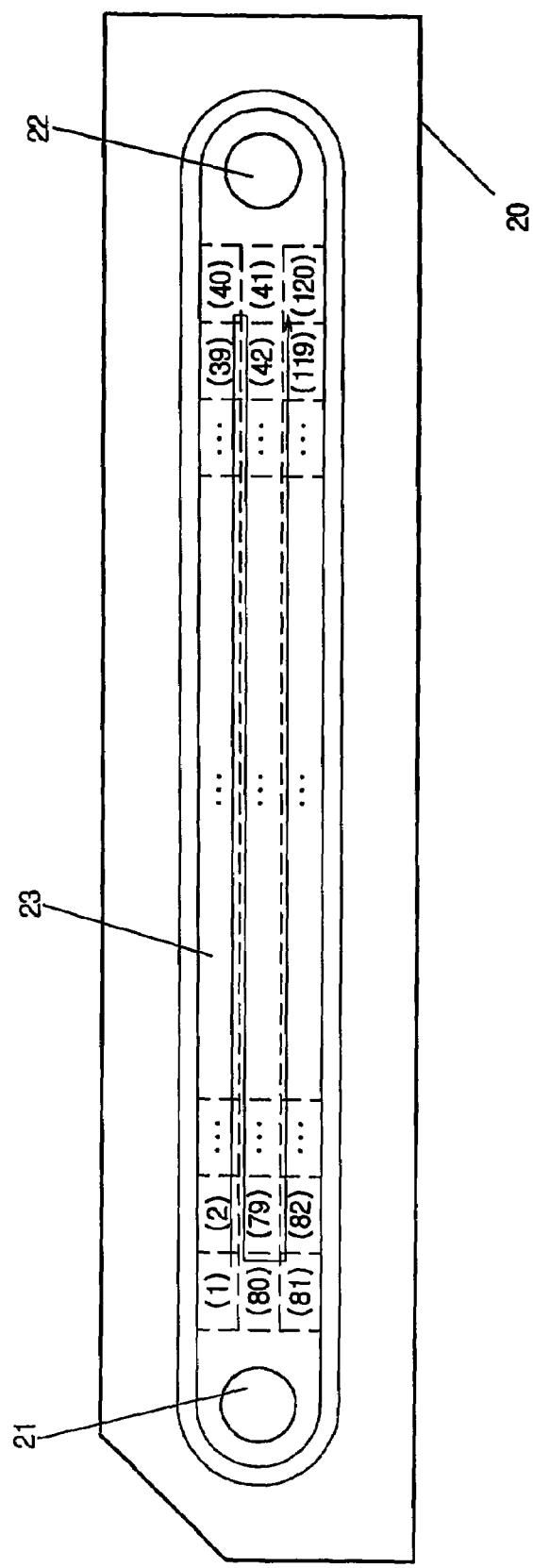
FIG. 3 is an embodiment dividing the sample chip into sub-areas in order that the micro-particle counting device photographs the sample chip by the sub-area and counts the particles in each of the sub-area.

FIG. 3 is an embodiment of partitioning the reading part into every sub-area so that the micro particle counting part can photograph the sample chip by the every sub-area and can count the particles. The sub-area (1) to (120) means each sub-area which may be photographed by the CCD camera individually. Therefore, the boundary line on the reading part does not actually exist, but it is a virtual line for convenience' sake of explanation. The area and the number of the sub-areas can be adjusted properly under consideration of the precision and the operation speed of counting micro-particle.

In case that the sample chip is divided into sub-areas as depicted in FIG. 3, the sub-area(1) is photographed and the sample chip is shifted in order that the sub-area(2) adjacent to the sub-area(1) photographed just before is shifted to the point where the light is incident and then the sub-area(2) is photographed. By repeating such processes, all the sub-area from sub-area (1) through (120) can be photographed.

The micro particle counting part counts micro particles on the sub-area photographed by the image photographing part, and then, calculates the total number of micro particles in the samples by adding the number of micro particles in each sub-area. Particularly in case that the height of the reading part wherein the sample is contained and the area of the sub-areas (1) through (120) photographed by the image photographing part are known, the volume of the reading part can be calculated. So, from the total volume of the sample and the total number of the micro particles, the average density of the micro particles(i.e, the number of micro particles in a unit volume).

Figure 4:
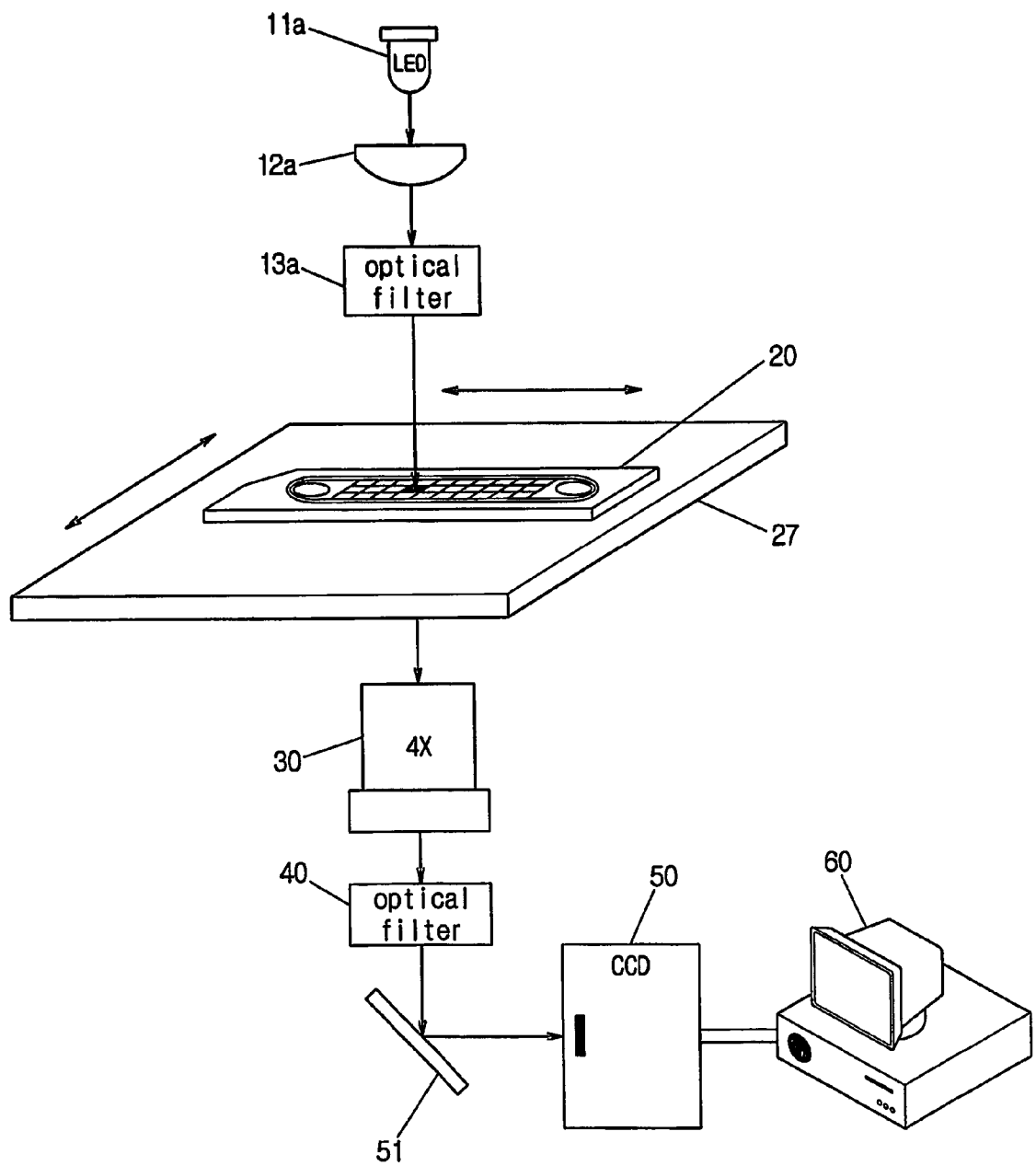
FIG. 4 is a component figure of the device with the light source of LED according to the first embodiment.

FIG. 4 depicts the first embodiment, which comprises the light source of LED. The device depicted in FIG. 4 is to count erythrocytes, which comprises:

a sample chip(20) wherein a sample containing the erythrocytes is located at the reading part with predetermined volume;

an LED(11a) projecting ultraviolet or visible light into a sub-area on the ample chip;

an incident light control lens(12a) controlling the amount of light emitted from the LED(11a) and the distance of focus, an incident optical filter(13a) which passes the light with a specified wave length passing the incident light control lens (12a), emits the light onto the sample chip;

an object lens(30) facing to the chip to magnify the image of the sample;

an optical filter(40) which passes the light with a specified wave length passing the object lens(30);

a CCD camera(50) photographing the image of the sample which passes the optical filter(40);

a micro particle counting part(60) counting erythrocytes in the sub-area photographed by the CCD camera(50); and a chip shifter(27) shifts the position of the sample chip in order that a certain area adjacent to the area photographed just before is shifted to the point where the light is incident.

The device further comprises the reflection mirror(51) to change the path of light in order that the light passing through the optical filter(40) is incident on the CCD camera(50).

Figure 5:
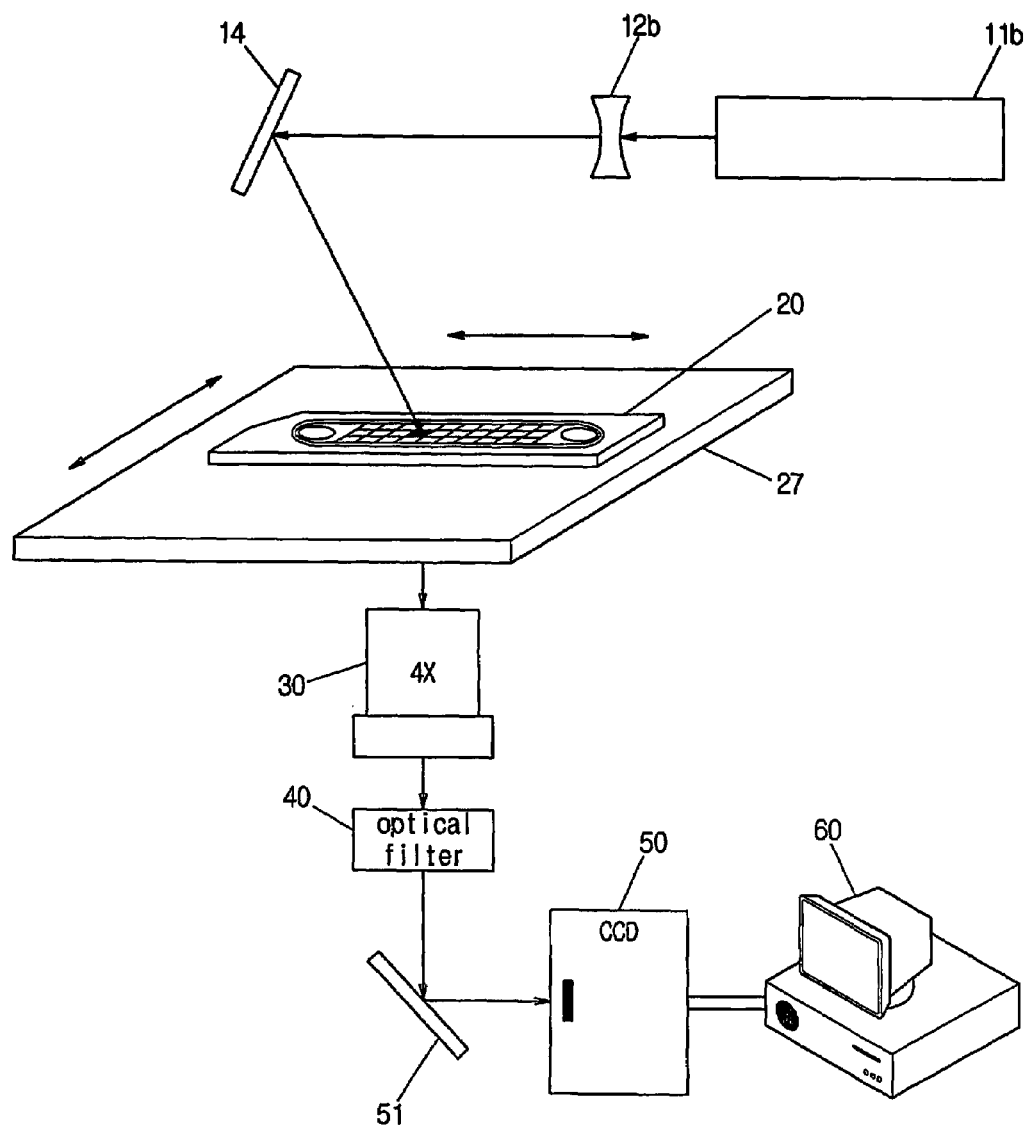
FIG. 5 is a component figure of the device with the light source of LASER according to the second embodiment.

FIG. 5 depicts the second embodiment, which comprises the light source of LASER(11b). The device depicted in FIG. 5 is to count cells containing a cell nucleus such as a leukocyte or somatic cell, which comprises:

a sample chip(20) wherein a sample containing cells and dyeing reagent at the reading part with predetermined volume;

a LASER source(11b) projecting light into a sub-area on the sample chip;

an incident light control lens(12b) controlling the amount of light emitted from the LASER source(11b) and the distance of focus, and emitting the light onto the sample chip;

an object lens(30) facing to the chip to magnify the image of the sample;

an optical filter(40) which passes the light with a specified wave length passing the object lens(30);

a CCD camera(50) photographing the image of the sample, which passes the optical filter(40);

a micro particle counting part(60) counting the cells on the sub-area photographed by the image photographing part; and a chip shifter(27) shifts the position of the sample chip in order that a certain area adjacent to the area photographed just before is shifted to the point where the light is incident.

This device further comprises a reflection mirror(14) to change the path of light in order that the light passing through the incident light control lens(12b) is incident on the sample chip(20), and another reflection mirror(51) to change the path of light in order that the light passing through the optical filter(40) is incident on the CCD camera(50).

If fluorescent dyeing reagent is applied to the inside of the sample chip(20) in advance, and then the sample chip(20) is filled with the sample, the CCD camera(50) may photograph specific particles by the optical filter(40) which may pass the light corresponding to the wave length of fluorescent dyeing reagent among the light passed the object lens(30).

Figure 6A:
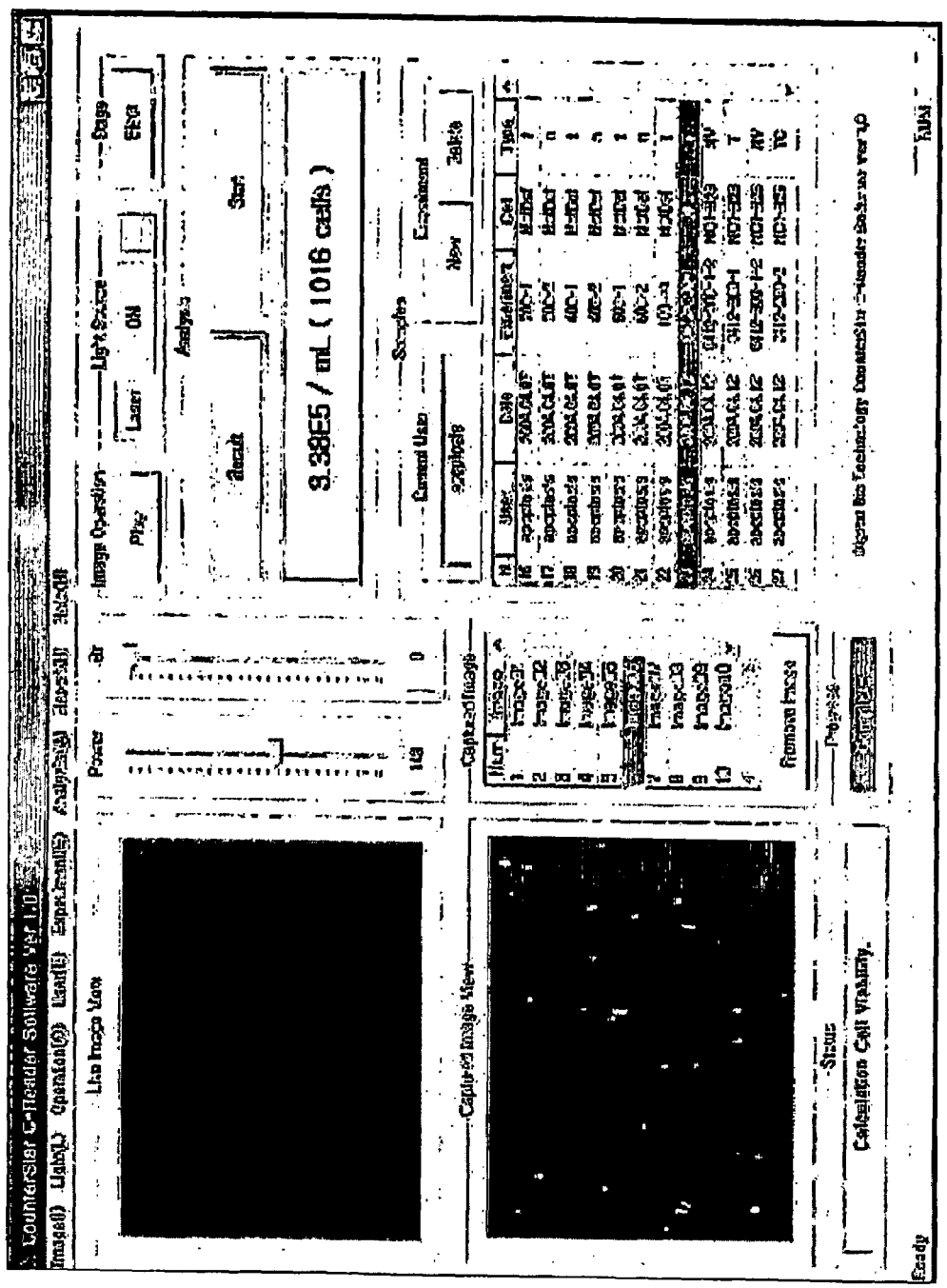
FIG. 6a and FIG. 6b is a result of counting cells and a graph using the device according to the second embodiment.

FIG. 6a depicts the experiment result of counting the number of animal cells in the sample in the sample chip by using the micro-particle counting device depicted in FIG. 4.

At first, animal cells are cultured in culture solution, an 20 μl of the sample is mixed with the same volume of dyeing solution including fluorescent dye, PI(Propidium Iodide) in order to dye the sample. Then, the dyed sample is filled in the sample chip by injecting the 20 μl of the dyed sample into the sample input hole using a pipette.

In the experiment, the micro-particle counting device divides the reading part of the sample chip into 120 sub-areas (3×40), photographs each sub-area, and counts the particles successively. The size of the sub-area is 0.82 mm wide and 0.61 mm long. The image depicted at the left-below side of FIG. 6a is a picture of the 6-th sub-area of the sample chip. In the picture, white spots represent animal cells that emit fluorescent light with a specific wavelength.

For all the 120 sub-areas, each photographed image is analyzed and micro particles in each sub-area are counted. By adding up them, the total number of the animal cells is 1016. Since the area of the photographed area in the reading part in the sample chip is 60 mm$^2$ and the height of the reading part is 100 μm, the volume of the observed sample is 6 μl. Thus, the average density of the animal cells in the sample is calculated at $1.69\times10^5$ particle/ml. As the sample is diluted by mixing the sample including animal cells with the sample dying solution in 1:1, the real density is $3.38\times10^5$ particle/ml by multiplying 2 of dilution factor.

Figure 6B:
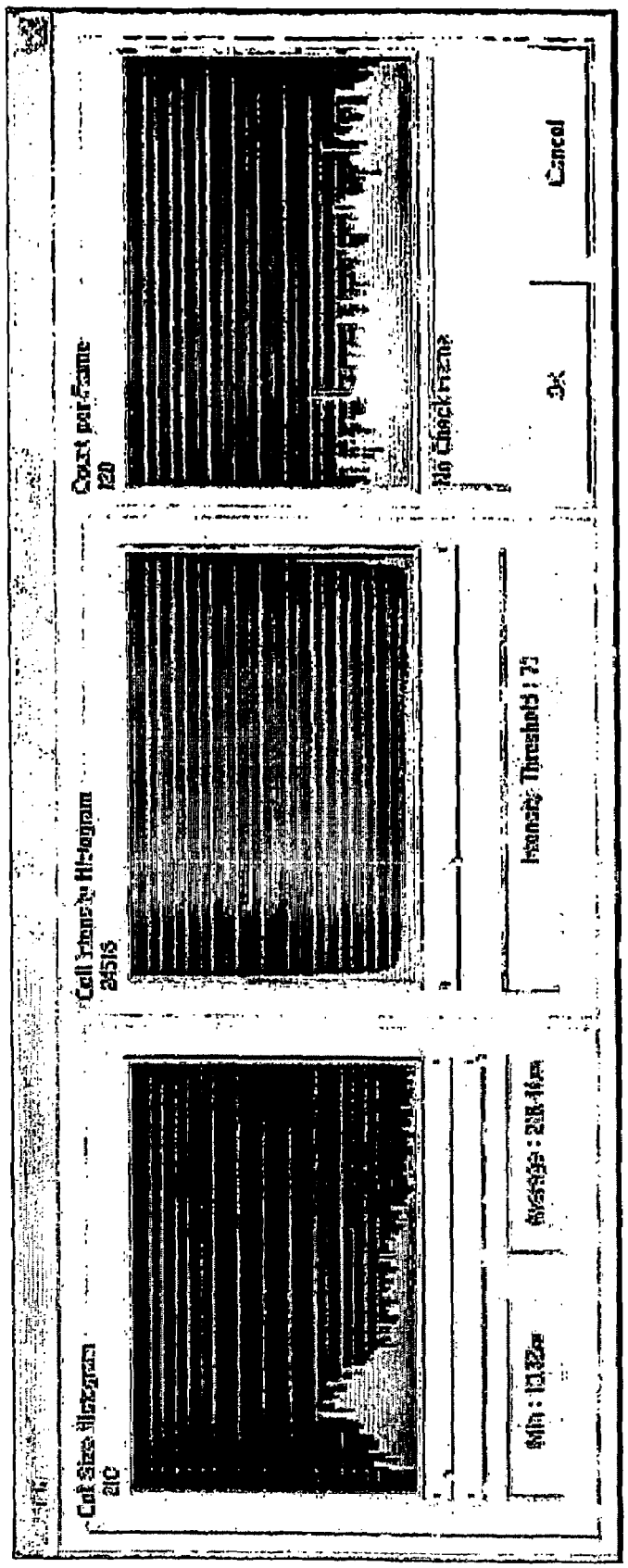

FIG. 6b is a graph which depicts the size of cell, the strength of fluorescence, and the number of cells in each image acquired by analyzing each of 120 photographed images.

The left graph depicts the distribution of the size of cells. The x-axis denotes the cell size displayed in the image, and the y-axis denotes the number of cells. It is preferable to set the x-axis value of peak as the maximum value of the cell size and the x-axis value of the left of the peak as minimum value of the cell size. As it is likely to count the pixels of noises as cells, it is preferable to set the minimum value to more than 4 micrometer.

The middle graph depicts the strength of fluorescence the cells emit. The x-axis denotes the strength of fluorescence displayed by the gray scale with range of 0 to 255, and the y-axis denotes the number of pixels corresponding to the strength of fluorescence. The pixel of gray scale 255 is the one where cells emit fluorescence, and the pixel of gray scale 0 is the one of a space. Therefore, most of gray scale values of pixels are 0 or else 255.

The right graph depicts the number of cells counted in each of 120 images. By adding up the number of cells showed in each image, the total number of cells that exist in the reading part of the sample chip can be acquired. Although there is variation about the number of cells in each image, there is no error by the variation because the numbers of cells in total image are added up.

The embodiments previously said are not confined to the description, but can be practiced in alternative, adjustment, and change within the range of being obvious to a skilled person in the art.

INDUSTRIAL APPLICABILITY

By using the micro-particle counting device according to the present invention, it is possible to automatically count the number of micro particles in a sample, such as yeast, lactobacillus, zymogen, erythrocytes, leukocytes, or somatic cells. Particularly, the chip shifter shifts the position of the chip by a predetermined distance at every predetermined time interval in order that a certain area adjacent to the area photographed just before by a CCD camera is shifted to the point where the light is incident. Therefore, sub-areas on the chip are photographed successively. The counting part counts the number of micro particles in each sub-area, and adds them together to calculate the total number of micro particles in the samples. Therefore, it is possible to count micro particles in the sample promptly and accurately. The structure of the device is simple, it can be used conveniently, and the cost is low.

What is claimed is:

1. A device for counting the number of micro particles, which comprises:

a sample chip wherein a sample containing particles may be located at a reading part;

a light source that projects light into a sub-area on the sample chip;

an object lens facing to the chip to magnify the image of the sample that is formed on the sub-area by the light illuminated from the light source;

an image photographing part that photographs the image of the sample, which is magnified by the object lens, in a sub-area on the sample chip;

a micro particle counting part that counts micro particles on the sub-area from the image photographed by the image photographing part; and a chip shifter that shifts the position of the sample chip in order that a certain area adjacent to the area photographed just before is shifted to the point where the light is incident, wherein the chip shifter shifts the sample chip by a predetermined distance at every predetermined time interval, and the image photographing part subsequently photographs the image of a certain sub-area adjacent to the sub-area photographed just before as the sample chip is shifted, and wherein the micro particle counting part counts micro particles in the sub-area successively photographed by the image photographing part, adds the number of micro particles in each sub-area together, and calculates the total number of micro particles in the samples; and then, calculates the average density of the micro particles from the total volume of the reading part of the sample chip and the total number of the micro particles.

2. The device according to claim 1, further comprising an optical filter that passes the light with a specific wavelength among the light passing through the object lens.

3. The device according to claim 1 wherein the light source is selected from the group consisting of a halogen lamp, a xenon lamp, a mercury lamp, an LED, and a LASER.

4. The device according to claim 1, further comprising an incident light control lens controlling the amount of light emitted from the light source and the distance of focus, and illuminating on the sample chip.

5. A device for counting the number of erythrocyte, which comprises:
- a sample chip wherein a sample containing erythrocytes may be located at a reading part;
- a lamp or an LED that projects light into a sub-area on the sample chip;
- an object lens facing to the chip to magnify the image of the sample that is formed on the sub-area by the light illuminated from the lamp or the LED;
- a CCD camera that photographs the image of the sample which is magnified by the object lens, in a sub-area on the sample chip;
- a micro particle counting part that counts erythrocytes on the sub-area from the image photographed by the CCD camera; and
- a chip shifter that shifts the position of the sample chip in order that a certain area adjacent to the area photographed by the CCD camera just before is shifted to the point where the light is incident,
- wherein the chip shifter shifts the sample chip by a predetermined distance at every predetermined time interval, and the CCD camera subsequently photographs the image of a certain sub-area adjacent to the sub-area photographed just before as the sample chip is shifted, and
- wherein the micro particle counting part counts erythrocytes in the sub-area successively photographed by the CCD camera, adds the number of erythrocytes in each sub-area together, and calculates the total number of the erythrocytes in the samples; and then, calculates the average density of the erythrocytes from the total volume of the reading part of the sample chip and the total number of the erythrocytes.

6. The device according to claim 5, further comprising an optical filter that passes the light with a specific wavelength among the light passing through the object lens.

7. The device according to claim 5, further comprising an incident light control lens controlling the amount of light emitted from the light from the lamp or the LED and the distance of focus, and illuminating on the sample chip.

8. A device for counting the number of cells with cell nucleus, which comprises:
- a sample chip wherein a sample containing the cells and fluorescent dyeing reagent may be located at a reading part;
- a LASER source that projects light into a sub-area at the sample chip;
- an object lens facing to the chip to magnify the image of the sample that is formed on the sub-area by the light illuminated from the LASER source;
- a CCD camera that photographs the image of the sample, which is magnified through the object lens in a sub-area on the sample chip;
- a micro particle counting part that counts the cells on the sub-area from the image photographed by the CCD camera; and
- a chip shifter that shifts the position of the sample chip in order that a certain area adjacent to the area photographed by the CCD camera just before is shifted to the point where the light is incident,
- wherein the chip shifter shifts the sample chip by a predetermined distance at every predetermined time interval, and the CCD camera subsequently photographs the image of a certain sub-area adjacent to the sub-area photographed just before as the sample chip is shifted, and
- wherein the micro particle counting part counts cells in the sub-area successively photographed by the CCD camera, adds the number of cells in each sub-area together, and calculates the total number of the cells in the samples; and then, calculates the average density of the cells from the total volume of the reading part of the sample chip and the total number of the cells.

9. The device according to claim 8, further comprising an optical filter that passes the light with a specific wavelength among the light passing through the object lens.

10. The device according to claim 8, further comprising an incident light control lens controlling the amount of light emitted from the LASER source and the distance of focus, and illuminating on the sample chip.

* * * * *